(12) United States Patent
Ashton et al.

(10) Patent No.: US 11,096,736 B2
(45) Date of Patent: Aug. 24, 2021

(54) PERICARDIAL CATHETER WITH TEMPERATURE SENSING ARRAY

(71) Applicant: Biosense Webster (Israel) Ltd., Yokneam (IL)

(72) Inventors: John H. Ashton, Glendora, CA (US); Kelvin M. Chuu, Los Angeles, CA (US); Mark T. Stanley, Seal Beach, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 14/101,266

(22) Filed: Dec. 9, 2013

(65) Prior Publication Data
US 2015/0157381 A1 Jun. 11, 2015

(51) Int. Cl.
*A61B 18/14* (2006.01)
*A61B 18/00* (2006.01)
*A61M 25/01* (2006.01)

(52) U.S. Cl.
CPC .......... *A61B 18/00* (2013.01); *A61B 18/1492* (2013.01); *A61B 2018/00041* (2013.01); *A61B 2018/00577* (2013.01); *A61B 2018/00791* (2013.01); *A61B 2018/00797* (2013.01);
(Continued)

(58) Field of Classification Search
CPC .......... A61B 2017/00092; A61B 2018/00363; A61B 2018/00821
See application file for complete search history.

(56) References Cited

U.S. PATENT DOCUMENTS

| | | | |
|---|---|---|---|
| 4,770,173 A * | 9/1988 | Feucht | A61B 18/16 606/32 |
| 5,033,477 A | 7/1991 | Fogarty et al. | |
| 5,505,730 A | 4/1996 | Edwards | |

(Continued)

FOREIGN PATENT DOCUMENTS

| CN | 101856271 B | 1/2015 |
|---|---|---|
| CN | 103315806 B | 6/2017 |

(Continued)

OTHER PUBLICATIONS

EPO Search Report for EP Application No. 14196730.7 dated May 4, 2015, 4 pages.
(Continued)

*Primary Examiner* — Michael F Peffley
*Assistant Examiner* — Bo Ouyang
(74) *Attorney, Agent, or Firm* — Lewis Roca Rothgerber Christie LLP

(57) ABSTRACT

A catheter adapted for use in the pericardial sac to sense temperature of an ablation site and surrounding heart tissue within one of the heart's ventricles or atria via proximity with the epicardium in the pericardial sac, includes a catheter body and a temperature sensing array adapted for placement on and contact with the epicardium. The temperature sensing array may comprise a 2-D body, with a surface adapted to contact an area on the epicardial tissue or in pericardial space. The array may also comprise at least one finger member, each having at least one temperature sensing location. The array may further comprise an elongated body having a generally circular configuration, a distal portion of which is movable to a spirally inward position.

20 Claims, 14 Drawing Sheets

(52) U.S. Cl.
CPC ............... *A61B 2018/00821* (2013.01); *A61B 2018/00839* (2013.01); *A61M 25/0147* (2013.01)

(56) References Cited

U.S. PATENT DOCUMENTS

| | | | |
|---|---|---|---|
| 5,964,757 A | 10/1999 | Ponzi | |
| 6,171,306 B1 * | 1/2001 | Swanson | A61L 31/10 600/374 |
| 6,584,360 B2 * | 6/2003 | Francischelli | A61B 18/1402 606/41 |
| 7,344,533 B2 * | 3/2008 | Pearson et al. | 606/41 |
| 7,819,817 B2 | 10/2010 | Rahn | |
| 8,145,289 B2 | 3/2012 | Calabro' et al. | |
| 8,200,308 B2 | 6/2012 | Zhang et al. | |
| 8,287,532 B2 | 10/2012 | Carroll et al. | |
| 8,295,902 B2 * | 10/2012 | Salahieh | A61B 5/01 600/374 |
| 9,314,299 B2 | 4/2016 | Fang | |
| 2001/0023348 A1 | 9/2001 | Ashley et al. | |
| 2001/0039415 A1 | 11/2001 | Francischelli et al. | |
| 2003/0163127 A1 * | 8/2003 | Scheib | 606/41 |
| 2003/0195499 A1 * | 10/2003 | Prakash | A61B 18/18 606/33 |
| 2008/0091193 A1 * | 4/2008 | Kauphusman | A61B 18/1492 606/41 |
| 2008/0281310 A1 * | 11/2008 | Dunning | A61B 18/16 606/32 |
| 2010/0030098 A1 * | 2/2010 | Fojtik | A61B 5/015 600/549 |
| 2010/0292687 A1 | 11/2010 | Kauphusman et al. | |
| 2011/0034912 A1 * | 2/2011 | de Graff et al. | 606/21 |
| 2011/0034936 A1 | 2/2011 | Maloney | |
| 2011/0054287 A1 | 3/2011 | Schultz | |
| 2011/0054446 A1 | 3/2011 | Schultz | |
| 2012/0130366 A1 * | 5/2012 | Carroll | A61B 18/1492 606/41 |
| 2013/0253504 A1 * | 9/2013 | Fang | A61B 18/1492 606/41 |
| 2013/0274730 A1 * | 10/2013 | Anderson | A61B 18/18 606/33 |
| 2013/0274731 A1 * | 10/2013 | Anderson | A61B 18/1492 606/33 |
| 2013/0325000 A1 * | 12/2013 | Bates | A61B 18/1492 606/41 |

FOREIGN PATENT DOCUMENTS

| | | |
|---|---|---|
| EP | 1 820 464 A1 | 8/2007 |
| EP | 2 241 279 A1 | 10/2010 |
| JP | H 3-236833 A | 10/1991 |
| JP | 10-505252 | 5/1998 |
| JP | 2002 516134 | 6/2002 |
| JP | 2004-160084 | 6/2004 |
| JP | 2006-504473 A | 2/2006 |
| JP | 2012-98968 A | 5/2012 |
| JP | 2013-192948 | 9/2013 |
| WO | WO 96/00036 A1 | 1/1996 |
| WO | WO 99/60924 A1 | 12/1999 |
| WO | WO2004/039273 A2 | 5/2004 |
| WO | WO 2004/066814 A2 | 8/2004 |
| WO | WO 2004/067081 A2 | 8/2004 |

OTHER PUBLICATIONS

European Search Report for EP Application No. 16196734.4 dated Mar. 16, 2017, 6 pages.
CN Search Report issued in corresponding application No. CN 201410746387.5, 2 pages.
CN Office action 1 issued in corresponding application No. CN 201410746387.5, 8 pages.
CN Office action 2 issued in corresponding application No. CN 201410746387.5, 7 pages.
CN Office action 3 issued in corresponding application No. CN 201410746387.5, 11 pages.
CN Office action 4 issued in corresponding application No. CN 201410746387.5, 5 pages.
JP Decision of Refusal issued in corresponding application No. JP 2014-247729, dated Feb. 27, 2020, 1 page.
JP Notice of Reasons for Refusal issued in corresponding application No. JP 2014-247729, dated Aug. 2, 2019, 3 pages.
JP Notice of Reasons for Refusal issued in corresponding application No. JP 2014-247729, dated Aug. 29, 2018, 5 pages.

* cited by examiner

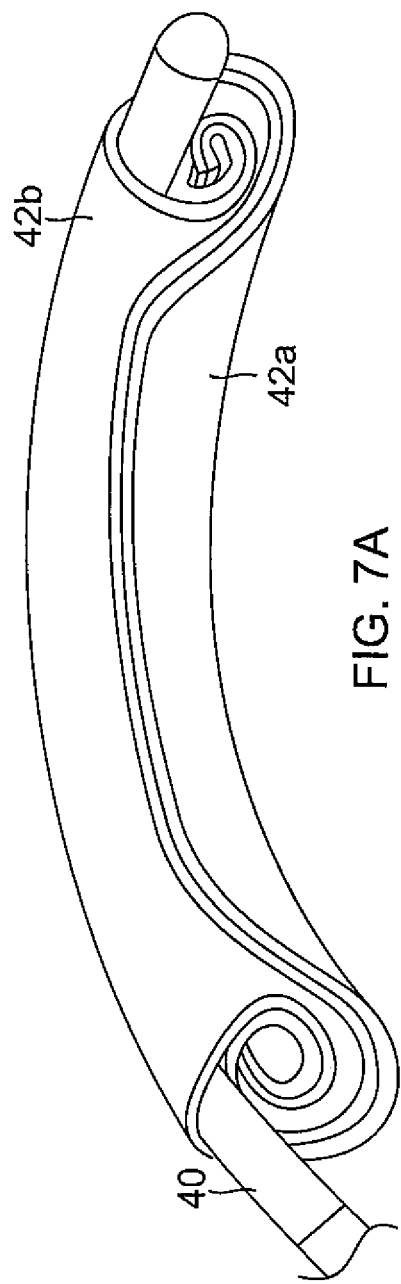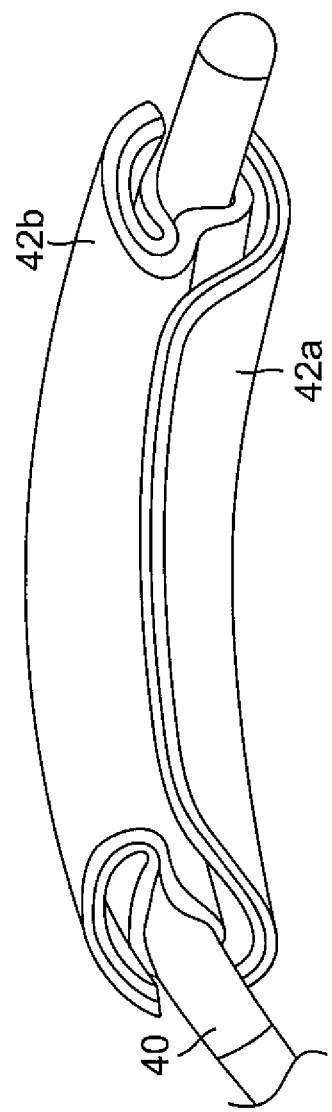
FIG. 7A
FIG. 7B

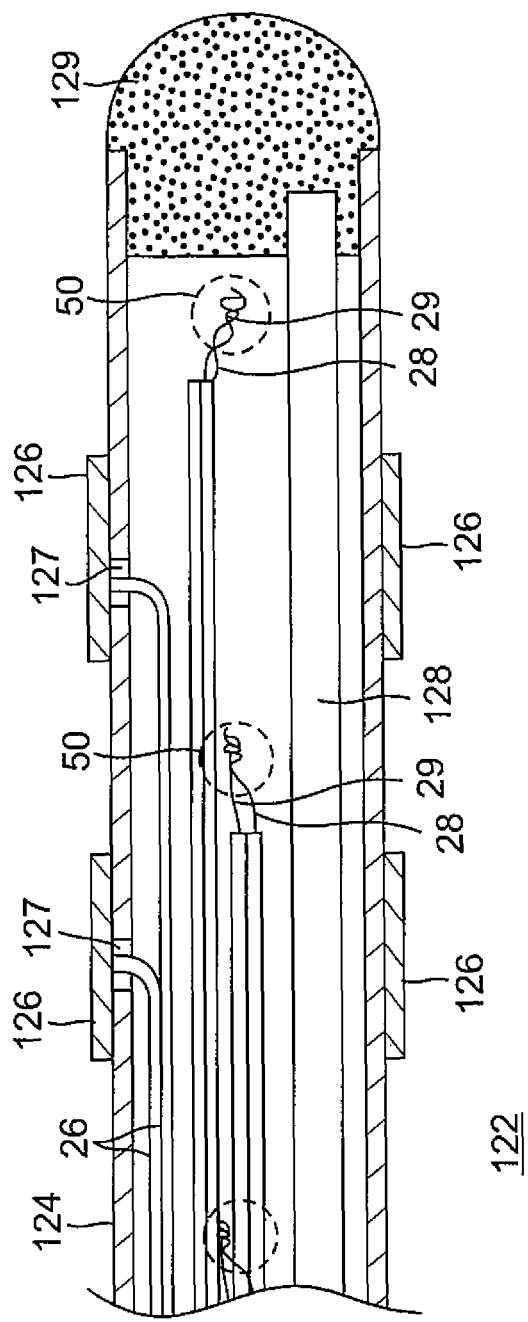

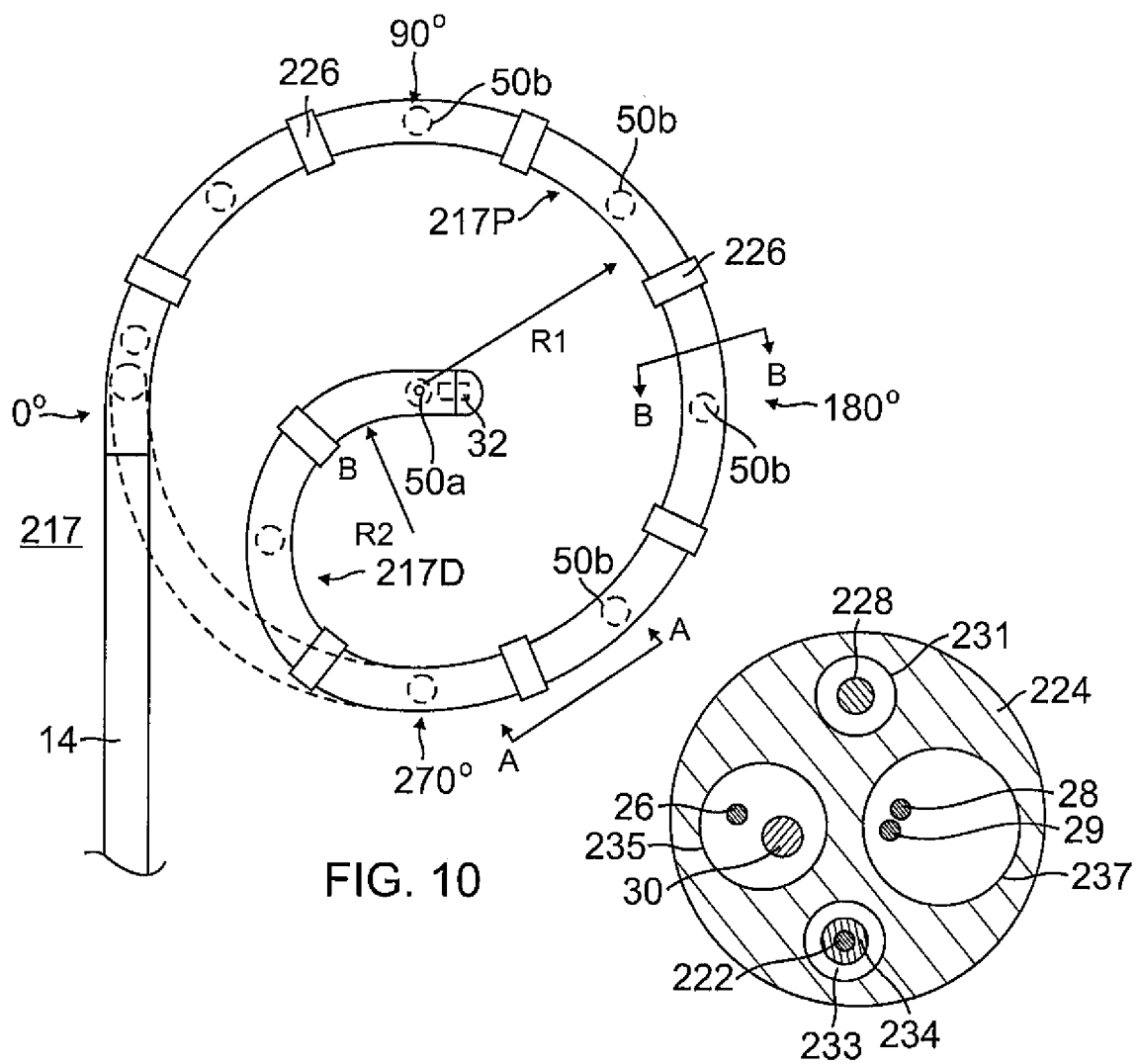
FIG. 10
FIG. 10B
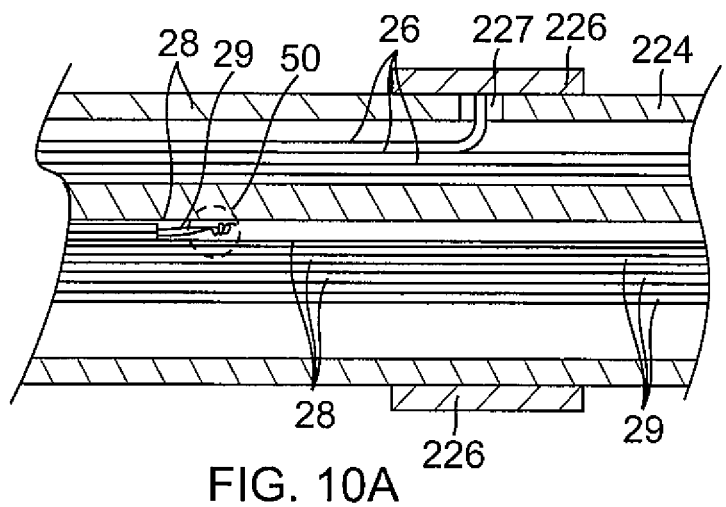
FIG. 10A

PERICARDIAL CATHETER WITH TEMPERATURE SENSING ARRAY

FIELD OF INVENTION

The present invention relates to a catheter that is particularly useful for temperature sensing.

BACKGROUND OF INVENTION

Cardiac arrythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion.

Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

Diagnosis and treatment of cardiac arrythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by heating local tissue to a temperature of irreversible damage, thereby forming non-conducting lesions. However, ablation at excessive temperature and/or for excessive duration can cause serious injury to heart and adjacent tissue, including perforation of the heart wall and damage to the esophagus or lungs. Often an electrophysiology mapping system, such as Carto® 3 (Biosense Webster), is used during the ablation procedure to map the heart anatomy and the locations of ablation and diagnostic catheters.

The heart comprises three tissue layers: endocardium, myocardium, and pericardium. The endocardium, the innermost layer, lines the hearts chambers and is bathed in blood. The myocardium is the thick middle layer of the heart with cells having specialized structures that help to rapidly conduct electrical impulses enabling the heart to contract. The pericardium includes the visceral pericardium (or epicardium) and the parietal pericardium. A pericardial cavity or space separates the epicardium and the parietal pericardium. Because resistive heating of tissue from ablation within an atrium or ventricle radiates outwardly from the myocardium, heating can be detected in the pericardial cavity.

Accordingly, it is desirable that a catheter be adapted for use in the pericardial sac by providing an array of temperature sensors for monitoring local tissue heating during ablation so as to prevent collateral damage to the epicardium, and adjacent tissue including the lungs or the esophagus. It is also desirable to monitor real-time lesion dimensions, such as depth and diameter, during the ablation to improve ablation efficacy and reduce adverse events.

SUMMARY OF THE INVENTION

The present invention is directed to a catheter adapted for use in the pericardial sac to sense temperature of an ablation site, and surrounding heart tissue, within one of the heart's ventricles or atria through contact with the epicardium and other areas of the pericardial sac. The catheter includes a catheter body and a temperature sensing array adapted for placement in the pericardial sac, either in or out of contact with the epicardial wall.

The catheter of the present invention may be placed on the epicardial wall, directly opposite of the ablation catheter across the cardiac wall, and used to monitor local tissue heating during ablation for various purposes, including, for example, detection of transmurality, mitigation of collateral damage and local tissue thickness. First, the present catheter can be used to detect transmurality by measuring when the epicardial wall has reached the temperature of irreversible tissue damage. Second, the present catheter can detect excessive heating to mitigate ablation damage to collateral tissue and organs, such as the lungs and esophagus. Third, tissue temperature sensed by the present catheter can be provided to an electrophysiology mapping system to estimate local tissue thickness at the ablation site, for example, by calculating the distance between the nearest portion of the present catheter and the ablation catheter. Fourth, tissue temperatures sensed by an array of temperature sensors on the present catheter and their local positions may be used in an algorithm which estimates the real-time lesion dimensions during an ablation. This algorithm may be incorporated into an electrophysiology mapping system, which may also include other ablation parameters to improve the algorithm accuracy, such as, for example, power, duration, contact force, impedance, stability, and local tissue thickness.

In one embodiment, the temperature sensing array comprises a 2-D body, with a surface adapted to contact an area on the epicardial tissue. The 2-D body has a top member, a bottom member and a longitudinal tubing sandwiched between. The 2-D body may include a support frame between the top and bottom member, and the support frame may provide the 2-D body with a predetermined curvature, such as concavity, for better conformity and contact with an outer surface of the epicardial tissue.

In one embodiment, the top and bottom members may be floppy and the support frame may be flexible and have shape memory to allow the 2-D body to be rolled into a tubular configuration for insertion into a guiding sheath and for deployment beyond a distal end of the guiding sheath at the temperature sensing tissue site.

The array carries a plurality of temperature sensing members, for example, thermocouple wire pairs, for sensing temperature at respective temperature sensing locations on the 2-D body of the array. In a more detailed embodiment, the thermocouple wire pairs extend through the tubing of the array with distal portions exiting the tubing via holes for placement between the top and bottom members.

In another embodiment, the array comprises a single or plurality of finger members, each having at least one temperature sensing location. Each finger members has a proximal end that extends from a tubular connector at a distal end of the catheter. In a detailed embodiment, the tubular connector is compressed so that the finger members "fan out", and the tubular connector has a curvature so that the finger members fan out over a curved area.

In another embodiment, the array comprises an elongated body having a generally circular configuration, a distal portion of which is movable to a spirally inward position. The array also includes a puller wire that extends through the elongated body and a compression coil that surrounds the coil and has a distal end proximal of the distal portion of the elongated body, such that proximal longitudinal movement of the puller wire relative to the elongated body causes the distal portion to the spirally inward position to as to position a temperature sensing location at or near a distal end of the distal portion to a more centered position relative to additional temperature sensing locations on the elongated body proximal to the distal portion.

BRIEF DESCRIPTION OF THE DRAWINGS

These and other features and advantages of the present invention will be better understood by reference to the following detailed description when considered in conjunction with the accompanying drawings wherein:

FIG. 7A is a perspective view of the array of FIG. 5, with a 2-D sensing body rolled in preparation for insertion into a guiding sheath, in accordance with one embodiment of the present invention.

FIG. 7B is a perspective view of the array of FIG. 5, with a 2-D sensing body rolled in preparation for insertion into a guiding sheath, in accordance with another embodiment of the present invention.

FIG. 8A is a side cross-sectional view of the array of FIG. 8, taken along line A-A.

FIG. 10 is a top plan view of a temperature sensing array, in accordance with another embodiment of the present invention.

FIG. 10A is a side cross-sectional view of the array of FIG. 10, taken along line A-A.

FIG. 10B is a longitudinal cross-sectional view of the array of FIG. 10, taken along line B-B.

DETAILED DESCRIPTION OF THE INVENTION

Figure 1:
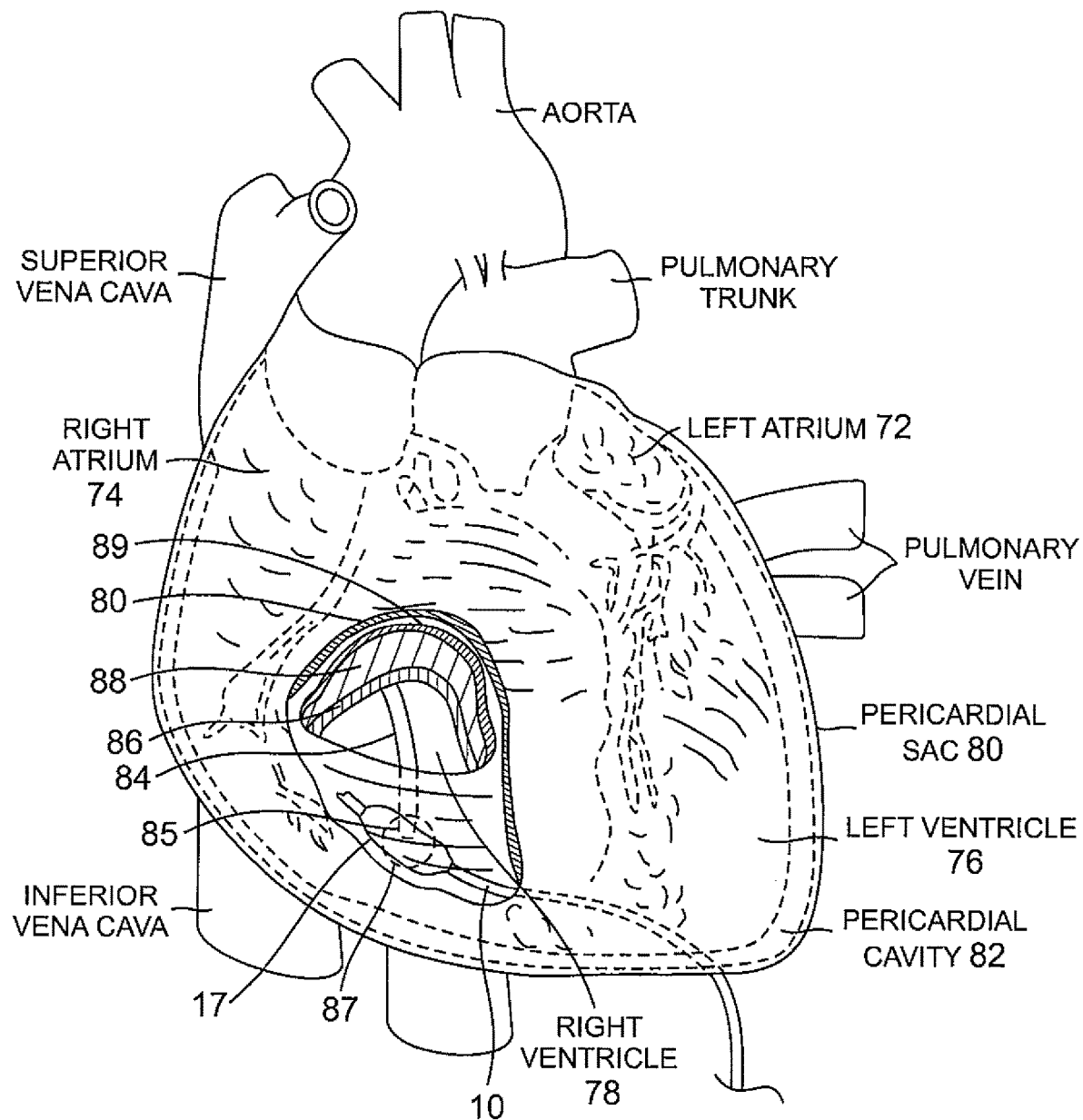
FIG. 1 is perspective view of a heart with an ablation catheter and a temperature sensing catheter of the present invention, in accordance one embodiment.

FIG. 1 illustrates a heart 70 with left atrium 72, right atrium 74, left ventricle 76 and right ventricle 78 that are enclosed in a pericardial sac 80 forming a pericardial cavity 82 surrounding the heart. An ablation catheter 84 is positioned in the heart, for example, in the right ventricle 78, with its ablation distal tip 85 in contact with endocardium 86 at a selected tissue ablation target site 87. Via a subxyphoid approach, an epicardial catheter 10 of the present invention is positioned inside of the pericardial sac 80, within the pericardial cavity 82, with its temperature sensing array 17 lying on or near an outer surface of epicardium 89 at a location generally opposite of the ablation distal tip 85 of the ablation catheter 84 such that the array 17 of the catheter 10 generally covers and spans over the ablation distal tip 85 so as to sense heat radiating outwardly from the ablation tissue target site 87 through endocardium 86 and myocardium 88.

Figure 2:
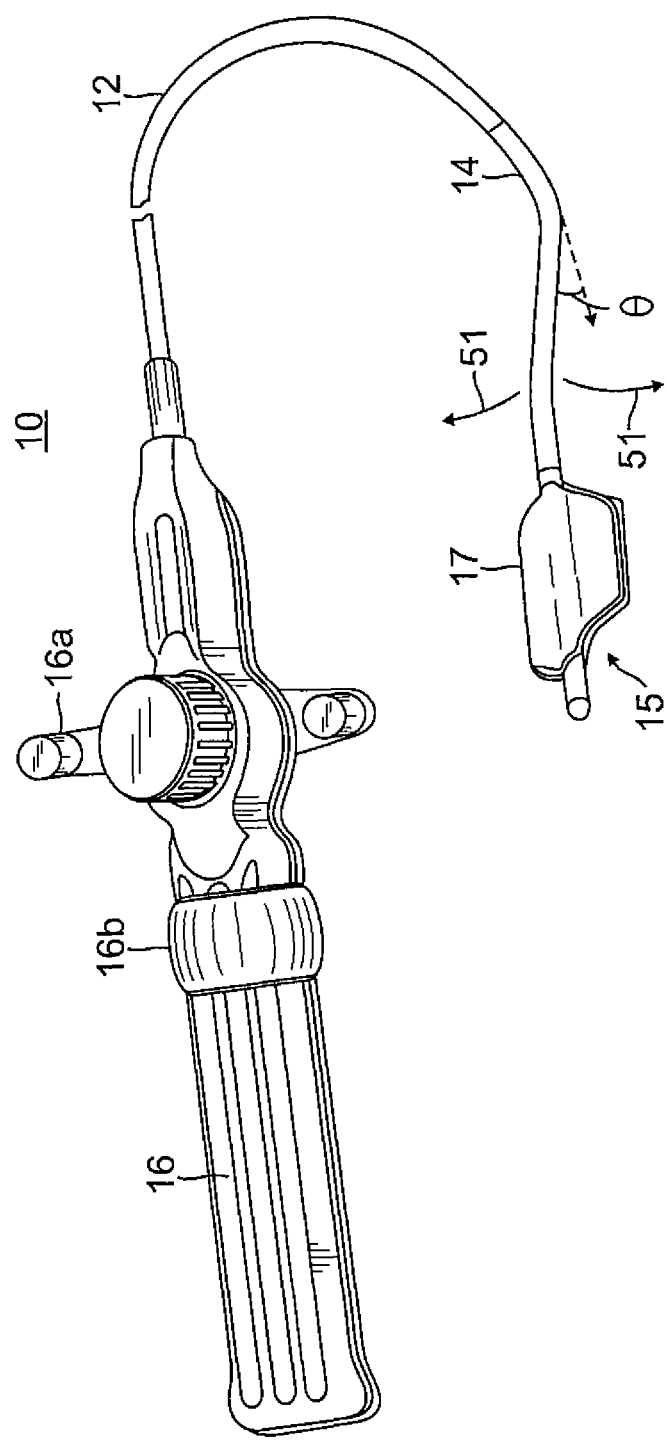
FIG. 2 is a perspective view of the temperature sensing catheter of FIG. 1.

As shown in FIG. 2, the catheter 10 has an elongated catheter body 12 with proximal and distal ends, an intermediate deflectable section 14 extending from the distal end of the catheter body 12, and a distal section 15 extending from the distal end of the intermediate section 14 which carries a temperature sensing array 17. The catheter also includes a control handle 16 at the proximal end of the catheter body 12 for controlling deflection of the intermediate section 14 via a first actuator 16. Advantageously, the temperature sensing array 17 has a 2-D body that provides a surface for contact with an area of tissue, including epicardium tissue.

Figure 3A:
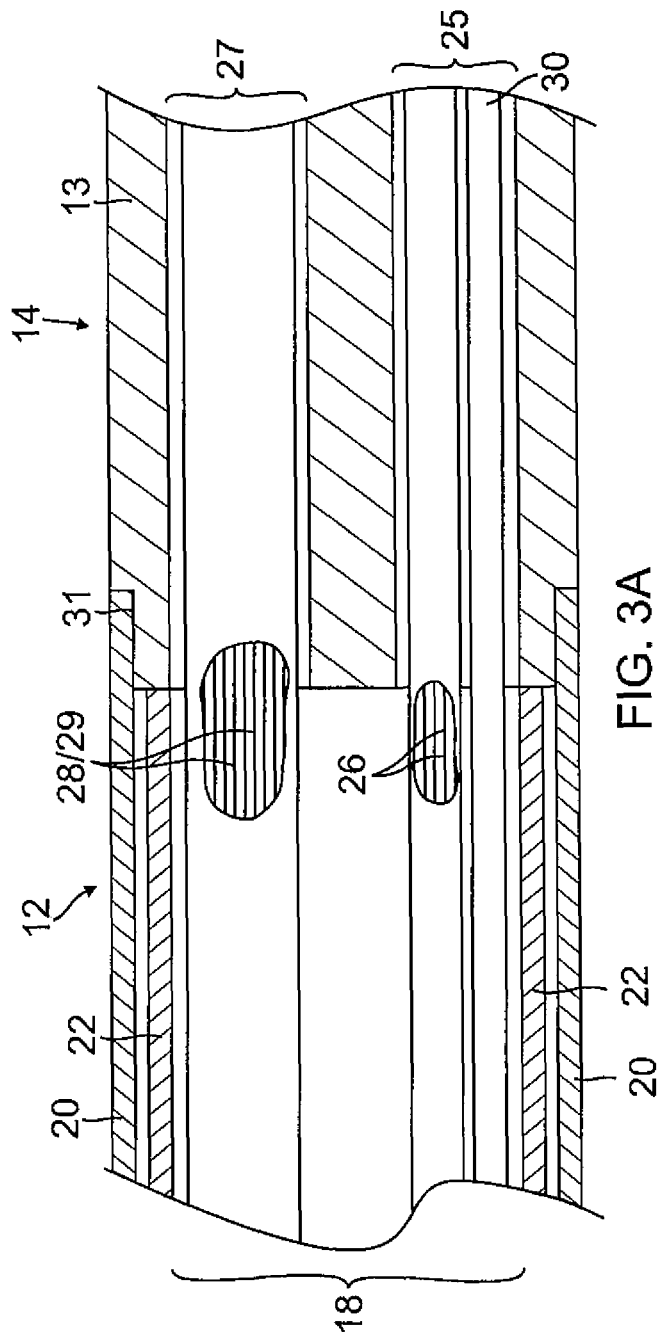
FIG. 3A is a side cross-sectional view of a junction between a catheter body and an intermediate section of the catheter of FIG. 2, taken along a first diameter.
Figure 3B:
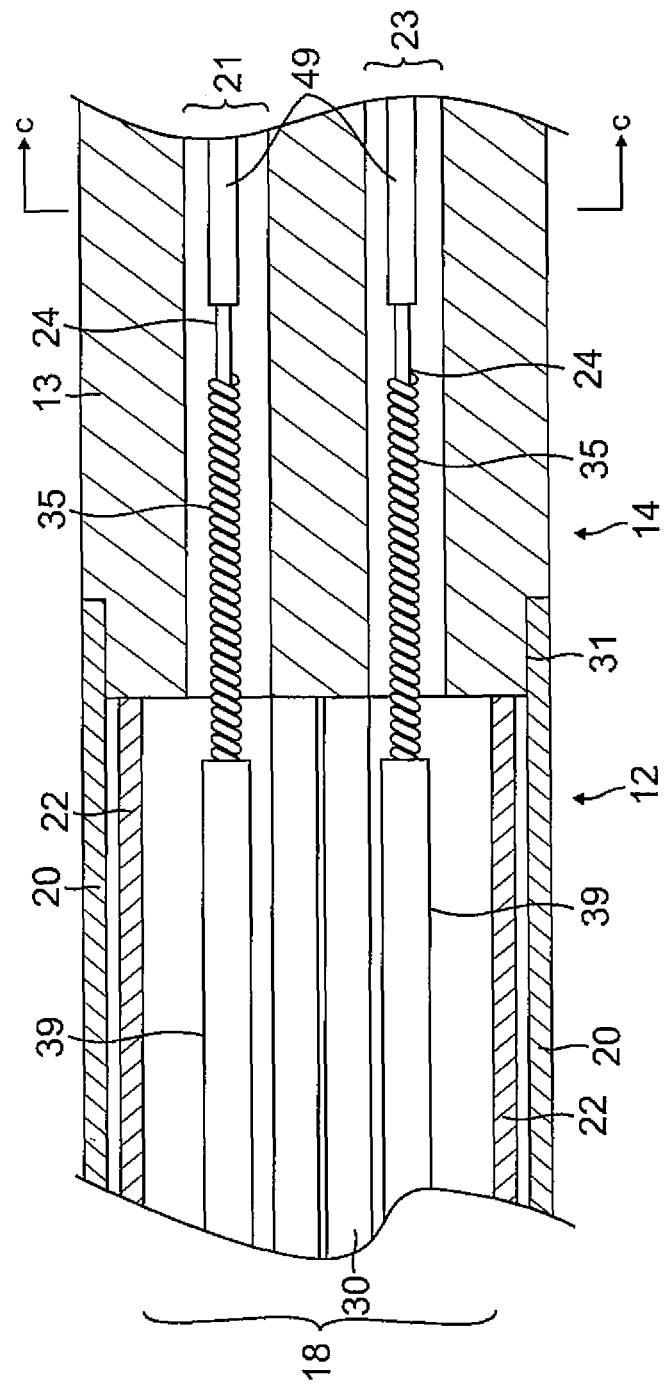
FIG. 3B is a side cross-sectional view of the junction between FIG. 3A, taken along a second diameter generally perpendicular to the first diameter.
Figure 3C:
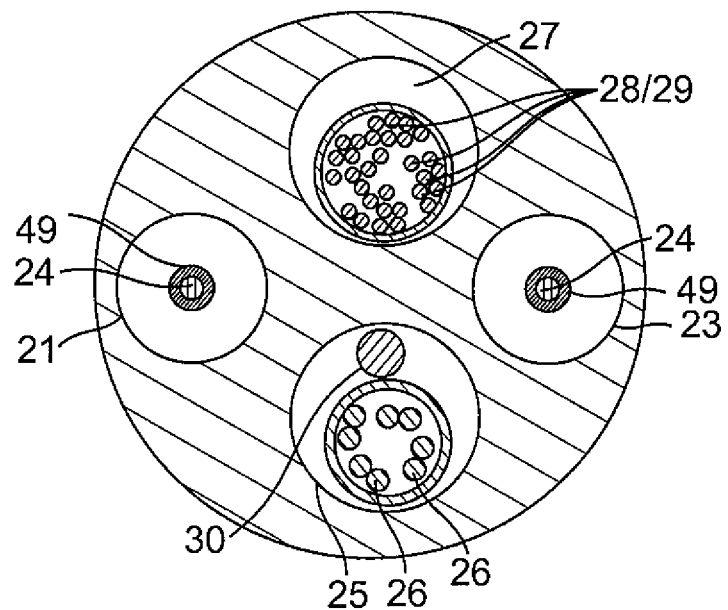
FIG. 3C is a longitudinal cross-sectional view of the intermediate section of FIG. 3B, taken along line C-C.

With reference to FIGS. 3A, 3B and 3C, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an embedded braided mesh of stainless steel or the like to increase torsional stiffness of the catheter body 12 so that, when the control handle 16 is rotated, the intermediate section 14 of the catheter 10 rotates in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller wires, lead wires, and any other desired wires, cables or tubings. If desired, the inner surface of the outer wall 20 is lined with a stiffening tube 22 to provide improved torsional stability. Glue joints (not shown) are provided to secure the stiffening tube 22 and the outer wall 20 to each other. They may be provided at the proximal and distal ends of the catheter body 12.

Components that extend between from the control handle 16 and into the central lumen 18 of the catheter body 12 include a plurality of thermocouple wire pairs 28 and 29 for the temperature sensing array 17, a cable 30 for an electromagnetic location sensor 32 housed in or near the temperature array 17, and a pair of puller wires 24 for deflecting the intermediate section 14.

Also illustrated in FIGS. 3A, 3B and 3C is an embodiment of the intermediate section 14 which comprises a shorter section of tubing 13. The tubing has a braided mesh construction with multiple off-axis lumens, for example lumens 21, 23, 25 and 27. Each of diametrically opposing first and second lumens 21 and 23 carries a respective puller wire 24 to enable bi-directional deflection of the catheter in two opposing directions within a plane (see arrows 51 in FIG. 2) to provide the catheter with, for example, a side-to-side "sweeping" motion that is well suited for movement in the pericardial cavity 82. Third lumen 25 carries the sensor cable 30 and fourth lumen 27 carries the thermocouple wire pairs 28 and 29. Additional lumens may be provided as needed.

The tubing 13 of the intermediate section 14 is made of a suitable non-toxic material that is preferably only slightly more flexible than the catheter body 12. A suitable material for the tubing 13 is braided polyurethane, i.e., polyurethane with an embedded mesh of braided stainless steel or the like. The size of each lumen is not critical so long as it is sufficient to house the respective components extending therethrough.

The useful length of the catheter, i.e., the shaft 12 and the intermediate section 14 that can be inserted into a patient's body excluding the assembly 17, can vary as desired. In one embodiment, the useful length ranges from about 110 cm to about 120 cm, more preferably about 115 cm to about 117 cm, and still more preferably about 116 cm. The length of the intermediate section 14 is a relatively small portion of the useful length, and preferably ranges from about 6.35 cm to about 7.62 cm, more preferably about 6.43 cm to about 6.5 cm, and still more preferably about 6.4 cm.

A means for attaching the catheter body 12 to the intermediate section 14 is illustrated in FIGS. 3A and 3B. The proximal end of the intermediate section 14 comprises an outer circumferential notch 31 that receives an inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

The puller wire 24 carried in each of the lumens 21 and 23 of the intermediate shaft 14 is preferably coated with Teflon®. The puller wires 24 can be made of any suitable metal, such as stainless steel or Nitinol, or a stronger material such as Vectran® nylon tubing, where the Teflon coating imparts lubricity to the puller wire. The puller wire preferably has a diameter ranging from about 0.006 to about 0.010 inch.

As shown in FIG. 3B, each puller wire 24 passes through a compression coil 35 in surrounding relation to its puller wire 24. The compression coil 35 extends generally from the proximal end of the catheter body 12 to the proximal end of the intermediate section 14 and may be secured at their proximal and distal ends respectively to the stiffening tube 22 and the proximal end of the intermediate section 14 by glue joints (not shown). The compression coil 35 is made of any suitable metal, preferably stainless steel, and is tightly wound on itself to provide flexibility, i.e., bending, but to resist compression. The inner diameter of the compression coil is preferably slightly larger than the diameter of the puller wire. Within the catheter body 12, the outer surface of the compression coil 35 is also covered by a flexible, non-conductive sheath 39, e.g., made of polyimide tubing. Within the intermediate section 14, each puller wire extends through a protective sheath 49 to prevent the puller wire from cutting into the tubing 13 of the intermediate section 14 during deflection.

Figure 4A:
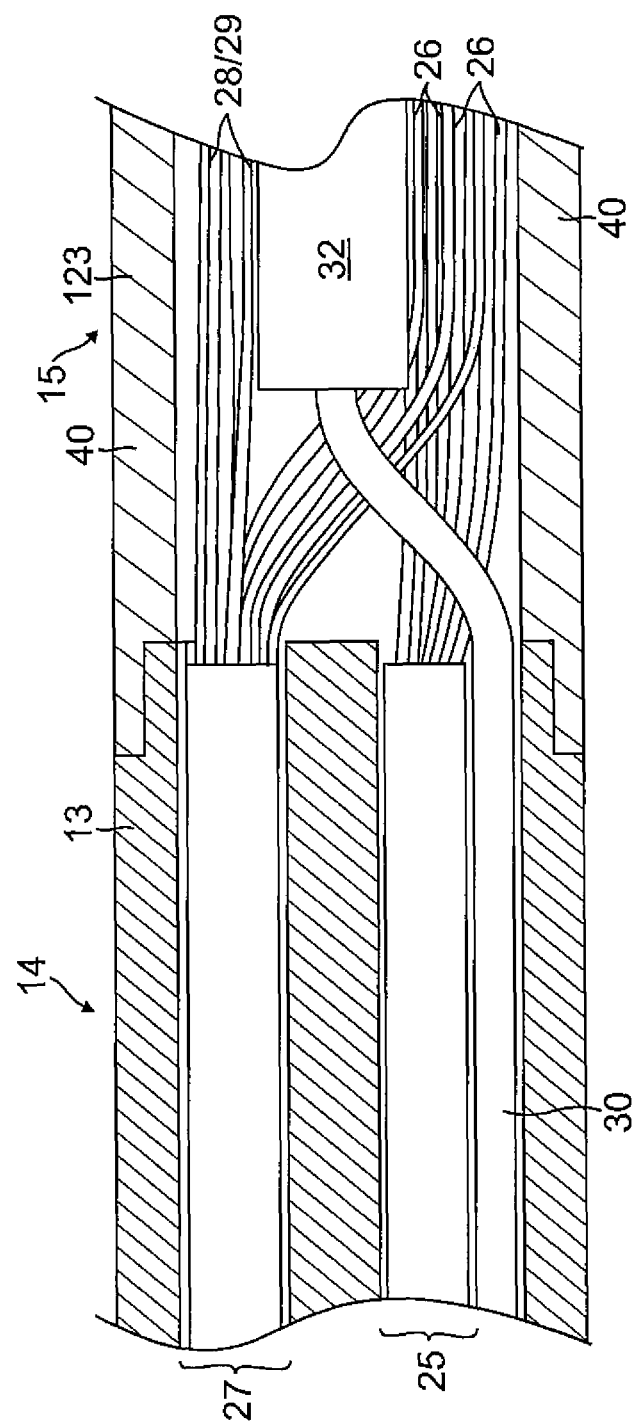
FIG. 4A is a side cross-sectional view of a junction between an intermediate section and a distal section of a temperature sensing catheter according to one embodiment, taken along one diameter.
Figure 4B:
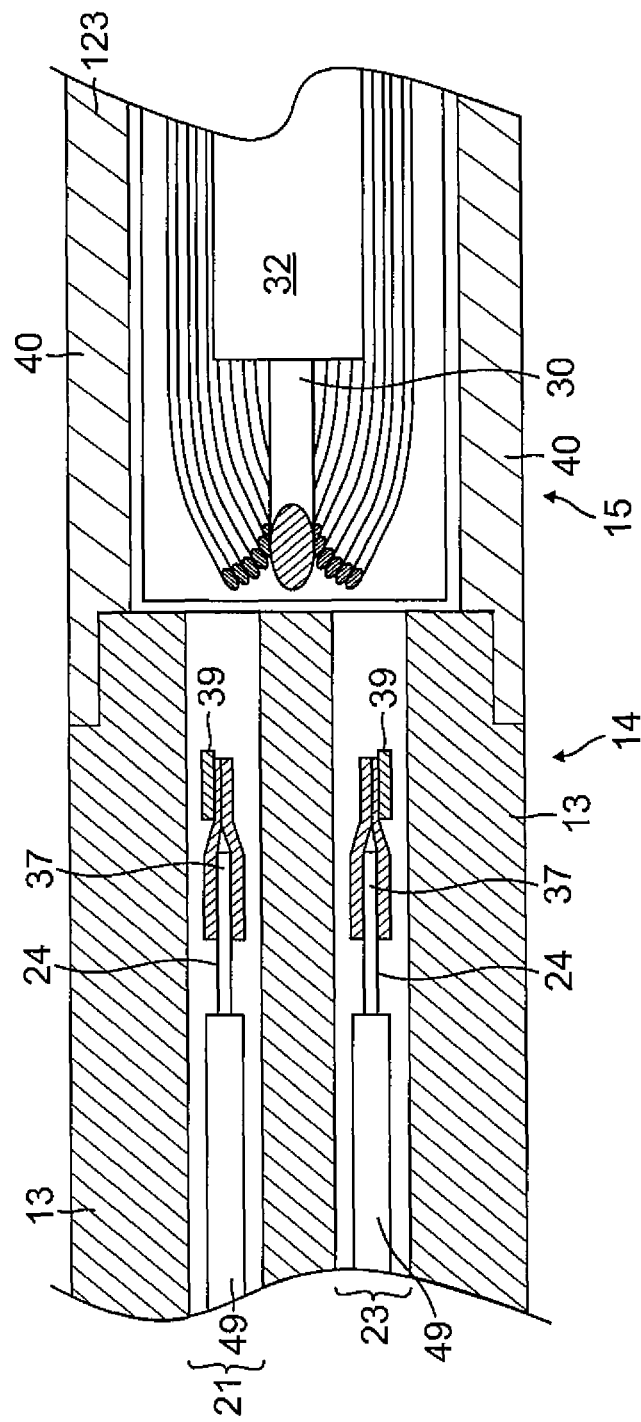
FIG. 4B is a side cross-sectional view of the junction of FIG. 4A, taken along a second diameter generally perpendicular to the first diameter.

Proximal ends of the puller wires 24 are anchored in the control handle 16. Distal ends of the puller wires 24 are anchored near the distal end of the tubing 13 of the intermediate section 14, as illustrated in FIG. 4B. Specifically, a T-shaped anchor is formed, which comprises a short piece of tubular stainless steel 37, e.g., hypodermic stock, which is fitted over the distal end of the puller wire 24 crimped to fixedly secure it to the puller wire. The distal end of the tubular stainless steel is fixedly attached, e.g., by welding, to a cross-piece 39 formed of stainless steel ribbon or the like. The cross-piece 39 extends through a hole (not shown) formed in the tubing 13 and because the cross-piece 39 is larger than the hole and, therefore, cannot be pulled through the hole, the cross-piece 39 anchors the distal end of the puller wire to the distal end of the intermediate section 14. As illustrated in FIG. 1, the deflectable intermediate section 14 is advantageously preformed with an angle θ near its distal end at so that the array 17 extends at an angle θ from the longitudinal axis of the intermediate deflectable section 14. This angle provides the intermediate deflectable section 14 and array 17 with a profile more conforming with the narrow and curved pericardial cavity 82. This angulation improves tissue contact by the array 17 to the outer surface of the epicardium 89. The angle θ can range between about 10 and 15 degrees, and more preferably between about 10 and 12 degrees. In accordance with a feature of the present invention, the bi-directional deflection of the electrode assembly 17 via the intermediate section 14 combined with the preformed bend of angle θ in a direction generally perpendicular to the plane of bi-directional deflection enables the electrode assembly 17 to adopt a side-to-side sweeping motion (arrows 51) that promotes tissue contact and conformity within the confines of the pericardial cavity 82. The angle θ can be formed into the tubing 13 as understood by one of ordinary in the art, including baking the tubing in a fixture.

Figure 5:
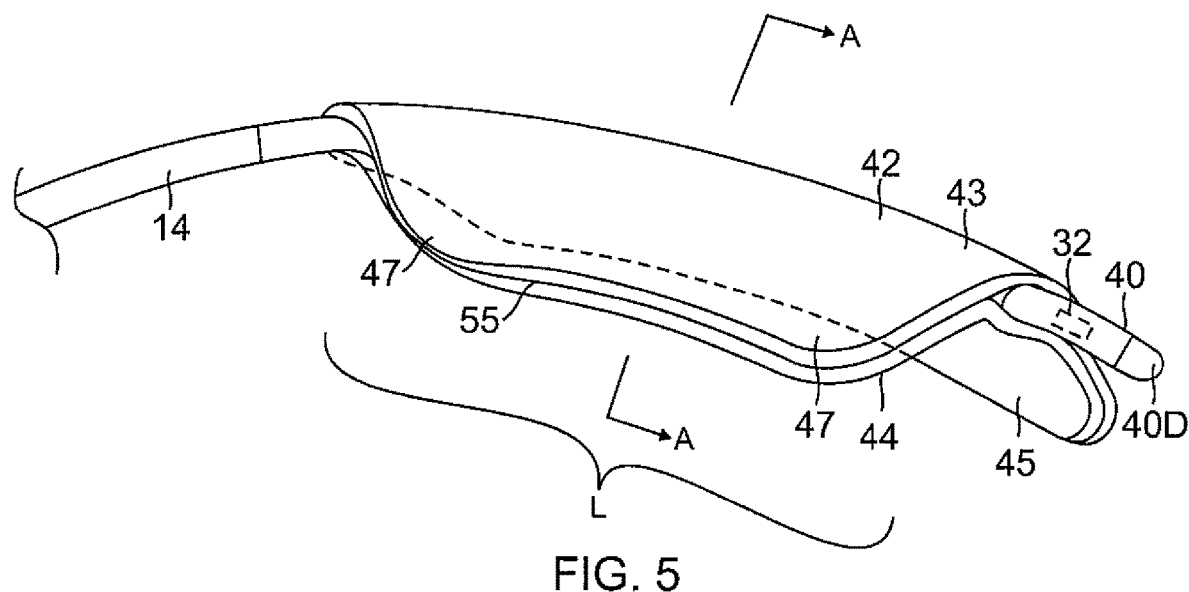
FIG. 5 is a detailed perspective view of a temperature sensing array of the catheter of FIG. 2.
Figure 5A:
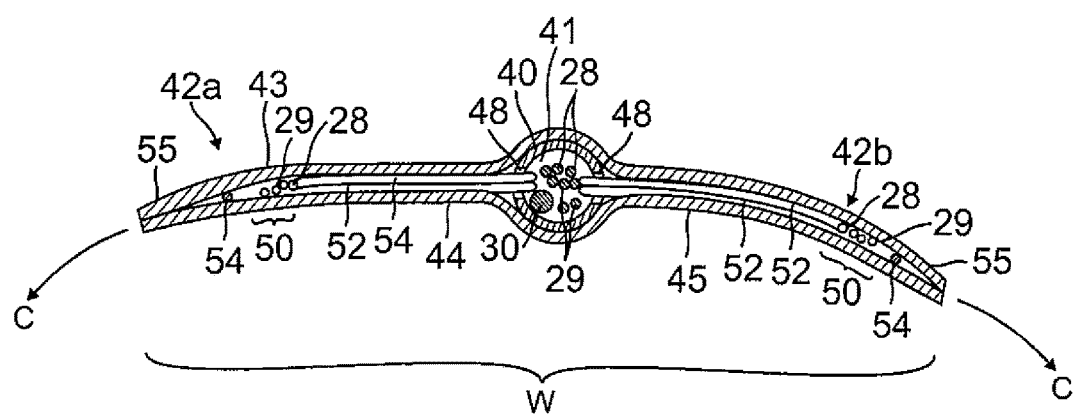
FIG. 5A is a longitudinal cross-sectional view of the array of FIG. 5, taken along line A-A.
Figure 6:
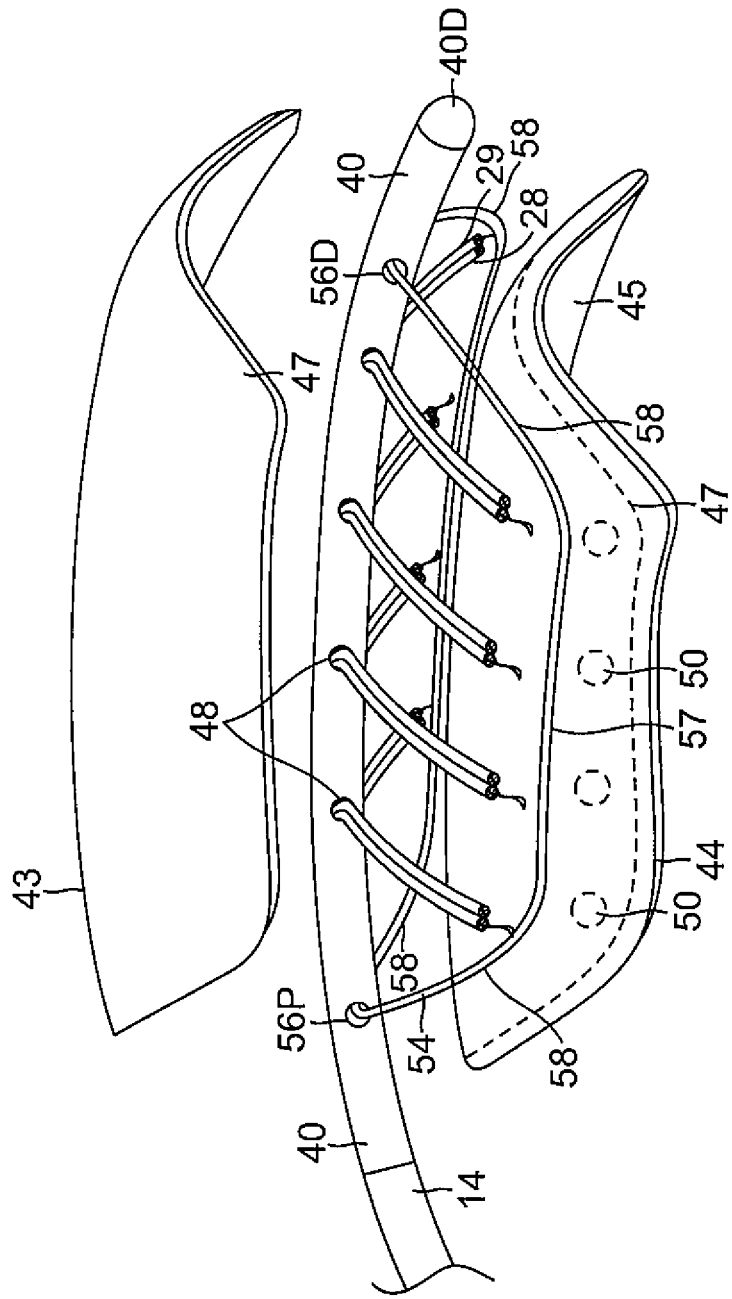
FIG. 6 is an exploded perspective view of the array of FIG. 5.

At the distal end of the intermediate section 14 is the temperature sensing array 17. In the illustrated embodiment of FIGS. 5, 5A and 6, the array 17 has an elongated longitudinal support member, for example, tubing 40, which supports a 2-D body 42 thereon. The tubing 40 extends distally from a distal end of the intermediate deflectable section 14 and can be attached thereto by any suitable means. In one embodiment, the tubing 40 has a single central lumen 41 and a distal end 40D that is sealed with a suitable material, e.g., polyurethane glue, formed into an atraumatic dome. The thermocouple wire pairs 28 and 29 extend from the lumen 27 of the intermediate section 14 and into the lumen 41. Distal portion of each thermocouple wire pairs passes to outside of the tubing 40 through a respective hole 48 formed in the side wall of the tubing 40. The sensor cable 30 extends from the lumen 25 of the intermediate section 14 and into the lumen 41 where a distal end of the sensor cable is attached to the location sensor 32 housed at or near the distal end of the tubing 40.

The array 17 also has first and second sheet members 43 and 44 which are stacked and affixed to each other by adhesive to form the 2-D body 42, with the tubing 40 sandwiched in between as a "spine" with opposing flaps or "wings" 42a and 42b extending therefrom. The body 42 has first and second surfaces, including a contact surface 45 adapted to lie on and make contact with an area of the outer surface of the epicardium 89. In the illustrated embodiment, the body 42 of the array 17 has a generally rectangular shape with a length L along the longitudinal axis defined by the tubing 40, and a width W. The length L may range between about 10 and 200 mm, and more preferably between about 25 and 75 mm. The width W may range between about 5 and 75 mm, and more preferably between about 40 mm and 60 mm. The body 42 of the array 17 has the tapered corners 47 so that the body 42 can be more easily fed into a guiding sheath (not shown) when passed through the patient's body and to minimize injury to the epicardium 89 and the pericardial sac 80 when the body 42 is deployed at the target site. The sheet members may be made of any suitable biocompatible material, including PEBAX and PELLETHANE.

As illustrated, the distal portion of each thermocouple wire pair 28 and 29 extends from a respective hole 48 perpendicularly (about 90 degree angle) to the tubing 40, although the angle can be varied as needed or desired. The tubing 40 has two rows of holes that extend longitudinally and are diametrically opposed to each other so that selected thermocouple wire pairs extend outwardly through one row on one side of the tubing and selected thermocouple wire pairs extend outwardly through another row from an opposite side of the tubing. The holes 48 of each row are generally equally spaced along the length of the tubing 40, although the spacing can be varied as needed or desired. The holes 48 of each row can be longitudinally aligned as illustrated, or alternatively they can be offset from each other. The length of each distal portion of the thermocouple wire pairs can be varied, or they can be equal, as needed or desired, so long as each pair is twisted together or otherwise joined at their distal ends to enable temperature-sensing function in accordance with the Seebeck effect, as understood by one of ordinary skill in the art. Accordingly, the twisted distal ends are placed at predetermined temperature sensing locations 50 on the body 42 for detecting temperature at those locations. Each wire of each thermocouple wire pair may be surrounded by a protective sheath 52 whose shorter length exposes the distal ends for joining. In the illustrated embodiment, the temperature array 17 has eight wire pairs, with four on each side of the tubing 40. It is understood that any suitable temperature sensing members may be used for sensing temperature at the locations 50, including, for example, thermistors.

To provide additional support to the array 17, a support frame 54 with shape memory may be affixed between the sheet members 43 and 44. In the illustrated embodiment, the support frame 54 generally extends along a peripheral edge 55 of the body 42 of the array 17, so that it has a matching configuration in terms of shape and size and it likewise has tapered corners. The frame 54 has two longitudinal sections 57 and two lateral sections 58. The lateral sections 58 can either pass over or under the tubing 40 or, alternatively, they pass through holes 56D and 56P formed in the tubing 40 that are distal and proximal, respectively, of the thermocouple wire pairs 28 and 29 and the holes 48.

The frame 54 is sufficiently flexible to allow the array 17 to be rolled about the tubing 40 (see FIGS. 7A and 7B) so that the array can be elastically coiled and compressed to pass through a guiding sheath. In the illustrated embodiment of FIG. 7A, flap 42a is coiled in one direction (e.g., counterclockwise) and flap 42b is wrapped around flap 42a in the opposite direction (e.g., clockwise). In the illustrated embodiment of FIG. 7B, the flaps 42a and 42b are wrapped around each other in the same direction (e.g., clockwise). Shape memory returns the frame 54 to its expanded configuration when outside the guiding sheath. The frame may also have a predetermined curvature (e.g., concavity) to allow better conformity with the epicardium (see arrows C in FIG. 5A). The frame may be constructed of any suitable material, for example, nitinol.

Figure 8:
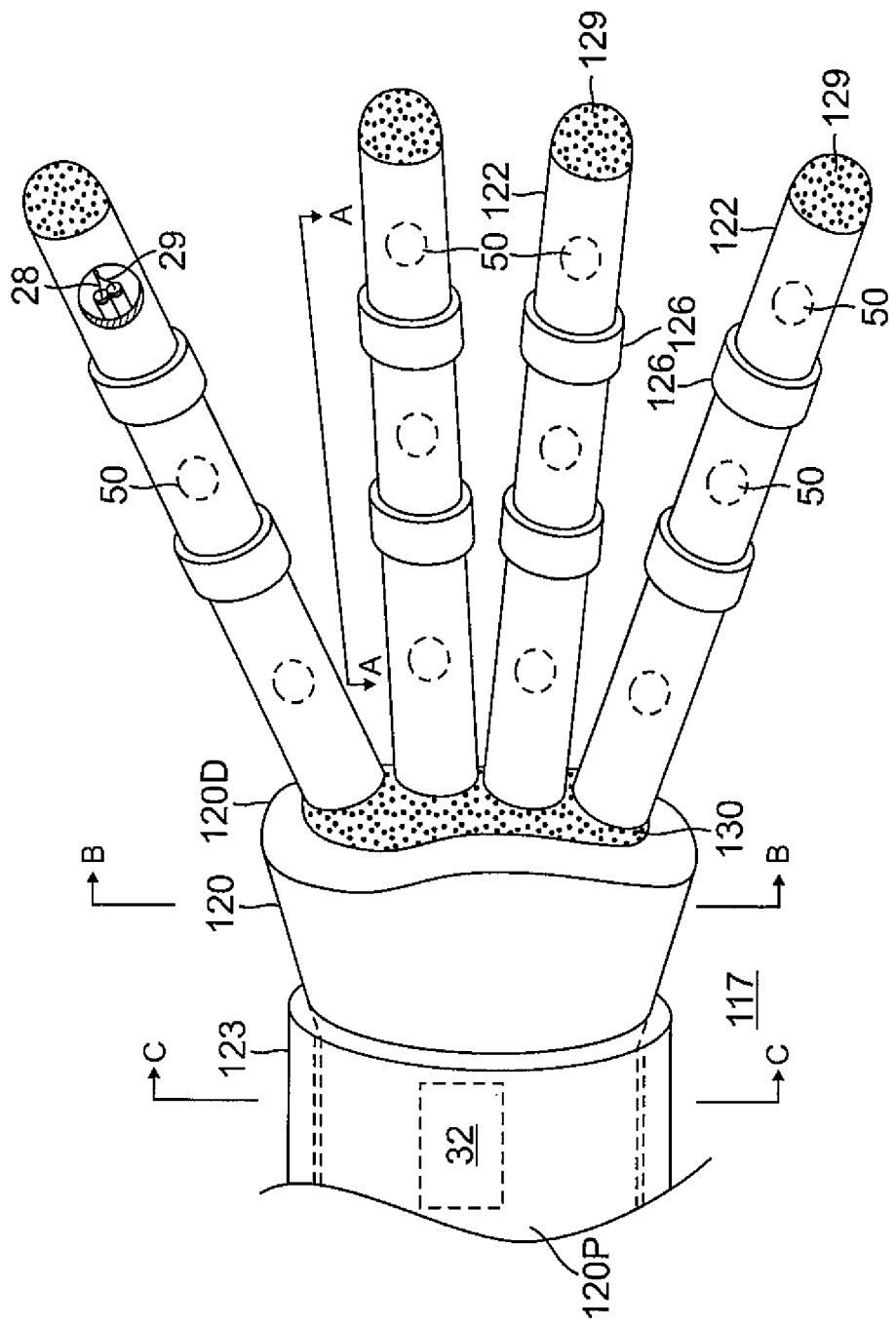
FIG. 8 is a perspective view of a temperature sensing array, in accordance with another embodiment of the present invention.
Figure 8C:
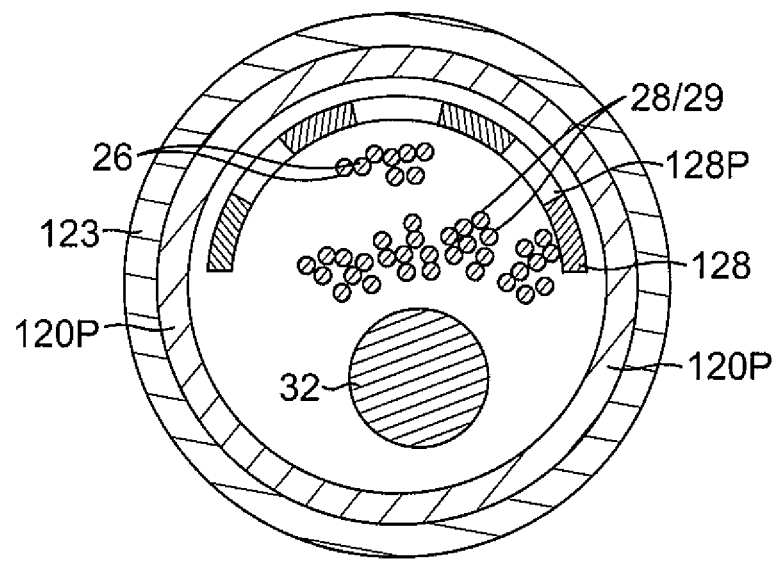
FIG. 8C is a longitudinal cross-sectional view of the array of FIG. 8, taken along line C-C.
Figure 8B:
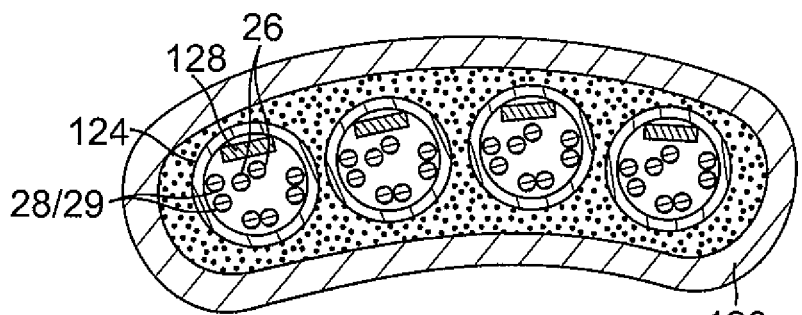
FIG. 8B is a longitudinal cross-sectional view of the array of FIG. 8, taken along line B-B.

In another embodiment as shown in FIGS. 8, 8A, 8B and 8C, a catheter 100 has a temperature sensing array 117 comprising a single or plurality of finger members 122 extending from a compressed short section of tubular stainless steel member 120, e.g., hypodermic stock, that helps feed the members 122 into a connector tubing 123 extending from the deflectable intermediate section 14. The connector tubing 123 houses the position sensor 32 (FIG. 8C) and allows lead wires 26 (FIG. 8A) for ring electrodes 126 and the thermocouple wire pairs 28 and 29 to reorient as needed as they extend into the array 117 (see FIGS. 4A and 4B). The tubular stainless steel member 120 has a proximal portion 120P with a circular cross-section that is inserted in the distal end of the tubing 123 (FIG. 8C). A distal portion 120D of the tubular stainless steel member 120 has a flattened oval cross-section (FIG. 8B) so that the finger members 122 fan out radially. The oval cross-section may have a slight curvature (as shown in FIG. 8B) so the finger members also fan out with a slight curvature, which allows for better contact with the epicardium.

Figure 9:
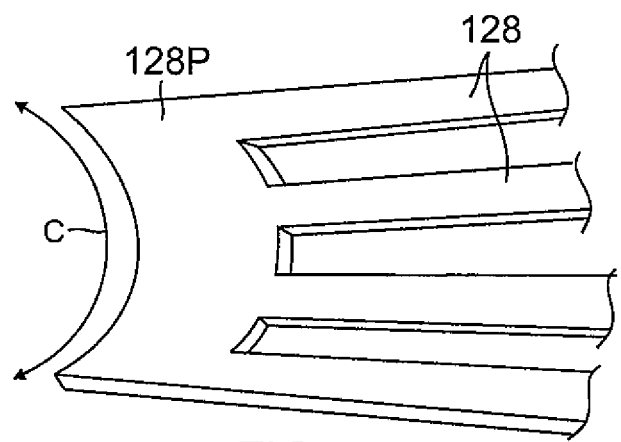
FIG. 9 is a perspective view of a support member as used in the array of FIG. 8.

As shown in FIG. 8A, each finger member 122 comprises a tubing 124 with a smaller diameter. The tubing has a central lumen 125 through which selected thermocouple wire pairs 28 and 29 and lead wires 26 extend to their respective sensing locations 50 or to their respective ring electrodes 126 via holes 127 formed in the side wall of the tubing 124 underneath the ring electrodes 126. Each finger member 122 may also include an elongated support member 128 with shape memory that extends longitudinally within the tubing 124. The support members 128 of the finger members 122 may all stem from a common proximal end 128P (FIG. 9) that is anchored in the tubular stainless steel member 120 (FIG. 8C). The support members 128 and the proximal end 128P may be formed (e.g., laser cut) from a single sheet of suitable material, e.g., nitinol, which may have a slight curvature C (FIG. 9). The proximal end 128P is potted in the compressed short section of tubing 120 by sealant 130. A distal end of each finger member 122 is sealed by sealant 129 formed into an atraumatic dome.

In another embodiment as shown in FIG. 10, a catheter 200 has a temperature sensing array 217 comprising an elongated body with a 2-D circular configuration lying generally within a plane. In accordance with a feature of the present invention, the body may be manipulated to assume a different configuration, for example, a spiral configuration with a main, generally circular proximal portion 217P and an inwardly extending or spiral distal portion 217D having a distal end that is advantageously positioned generally at a center of the generally circular configuration so that the array has at least one inner, centered temperature sensing location 50a that is surrounded by a plurality of outer temperature sensing locations 50b. As illustrated, the distal portion 217D is movable between a first position in alignment with the generally circular configuration (broken lines in FIG. 10) and a second position spirally inward of the generally circular configuration (solid lines in FIG. 10). In that regard, the catheter 200 can be positioned in the pericardial sac, in or out of contact with the epicardium 89, such that the inner temperature sensing location 50a is directly opposite of the ablation catheter 84 at a tissue ablation site within the heart and the outer temperature sensing locations 50b surround the site at a radial distance therefrom to measure a temperature difference or gradient of an area between the locations 50a and 50b.

With reference to FIGS. 10A and 10B, the array 217 comprises a section of tubing 224 with multiple lumens, at least one of which is off-axis. In the illustrated embodiment, the tubing 224 has four off-axis lumens 231, 233, 235 and 237. A support member 228 extends through the lumen 231. The lead wires 26 for ring electrodes 226 extend through the lumen 235. The thermocouple wire pairs 28 and 29 extend through the lumen 237. An additional puller wire 222 extends through the lumen 233. The support member 228 with shape memory, e.g., a nitinol wire, is configured to provide a generally circular configuration with a radius R1. The puller wire 222, which has a proximal end anchored in the control handle 16 and a distal end anchored in a distal end 240 of the array 217, has a distal portion that is surrounded by a compression coil 234 that has a distal end at or near a proximal end of the spiral distal portion. In the illustrated embodiment of FIG. 10, the generally circular main proximal portion extends between about 0 degrees and 270 degrees of the array 217, and thus the compression coil also extends between about 0 degrees and 270 degrees of the array 217. Accordingly, when the additional puller wire 222 is drawn proximally, a distal portion of the tubing 224 extending between about 270 to 360 degrees (distal of a distal end of the compression coil 234) achieves a tighter curvature with a radius R2 that is less than radius R1 to provide the array 217 with the inwardly spiral distal portion for positioning the temperature sensing location 50a at about the center of the circular configuration of radius R1. In that regard, the tubing 224 of the array 217 is oriented with the lumen 233 for the puller wire 222 being closest to the center of the main circular configuration 217P. Moreover, the lumen 233 may be aligned with either of the lumens 21 and 23 of the tubing 13 of the deflectable intermediate section 14 for the deflection puller wires 24a and 24b. To facilitate the array achieving the spiral configuration when the additional puller wire is drawn proximally, the tubing 224 may have greater flexibility (such as a lesser durometer) than the tubing 13 of the deflectable intermediate section 14.

Figure 3D:
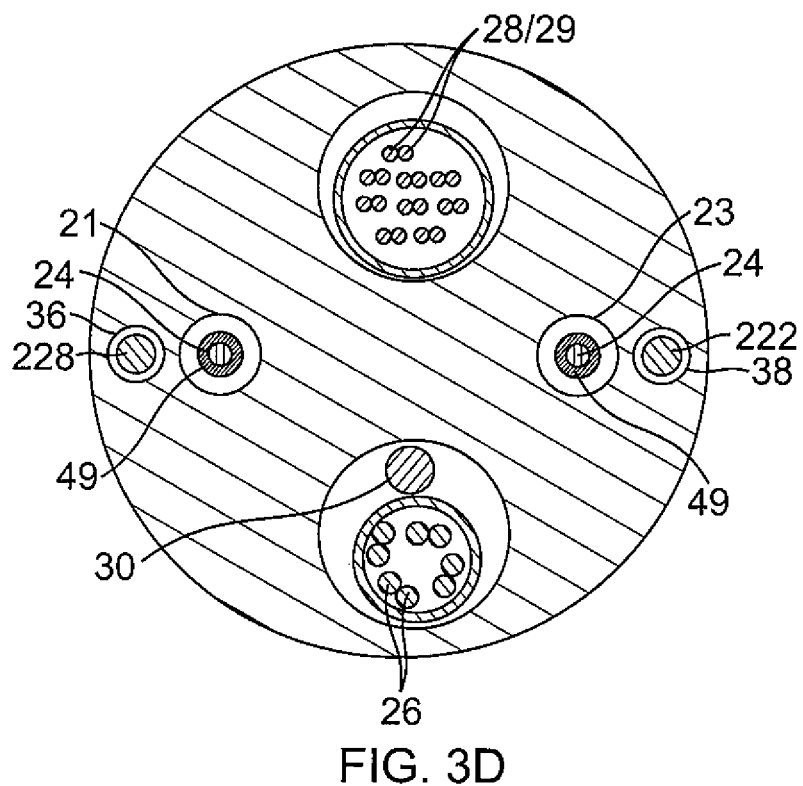
FIG. 3D is a longitudinal cross-sectional view of the intermediate section of a temperature sensing catheter according to an alternate embodiment.

The support member 228 extends at least the entire length of the array 217 and preferably a short distal proximally into the distal end of the deflectable intermediate section 14. The tubing 13 of the intermediate section 14 has a first additional lumen 36 for receiving a proximal end of the support member, as shown in FIG. 3D. The tubing 13 also has a second additional lumen 38 for receiving the puller wire 222, as also shown in FIG. 3D.

A proximal end of the puller wire 222 is also anchored in the control handle 16 which may have a second actuator 16b (FIG. 2) for manipulating the additional puller wire 222.

Control handles with multiple puller wire actuators are known, including those described in U.S. application Ser. No. 12/550,204, filed Aug. 28, 2009, entitled CATHETER WITH MULTI-FUNCTIONAL CONTROL HANDLE HAVING LINEAR MECHANISM and U.S. application Ser. No. 12/550,307, filed Aug. 28, 2009, entitled CATHETER WITH MULTI-FUNCTIONAL CONTROL HANDLE HAVING ROTATIONAL MECHANISM, the entire disclosures of which are hereby incorporated by reference.

The tubings of the deflectable intermediate section 14 and of the various aforementioned temperature sensing arrays 17, 117 and 217 can be made of any suitable material that is flexible and biocompatible and preferably plastic, such as polyurethane or PEBAX. The aforementioned shape memory support members 54, 128 and 228 can be straightened or bent out of their original shapes upon exertion of a force and are capable of substantially returning to their original shapes upon removal of the force. A suitable material for the shape memory elements is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability.

The ring electrodes 126 are electrically connected to an appropriate mapping or monitoring system (not shown) via the lead wires 26, each of which has its proximal end terminating in a connector at the proximal end of the control handle 16. The electrode lead wires extend through the central lumen 18 in the catheter body 12, and through the lumen 25 of the intermediate section 14. The portion of the lead wires extending through the central lumen 18 of the catheter body 12, and proximal end of the lumen 24 can be enclosed within a protective sheath (not shown), which can be made of any suitable material, preferably polyimide.

Each lead wire is attached to its corresponding ring electrode by any suitable method. A preferred method for attaching a lead wire to a ring electrode involves first making a small hole through the wall of the non-conductive tubing. Such a hole can be created, for example, by inserting a needle through the non-conductive covering sufficiently to form a permanent hole. The lead wire is then drawn through the hole by using a microhook or the like. The end of the lead wire is then stripped of any coating and welded to the underside of the ring electrode, which is then slid into position over the hole and fixed in place with polyurethane glue or the like. Alternatively, each ring electrode is formed by wrapping a lead wire around the non-conductive covering a number of times and stripping the lead wire of its own insulated coating on its outwardly facing surfaces.

The ring electrodes can be made of any suitable solid conductive material, such as platinum or gold, preferably a combination of platinum and iridium. The ring electrodes can be mounted onto the tubing with glue or the like. Alternatively, the ring electrodes can be formed by coating the tubing with an electrically conducting material, like platinum, gold and/or iridium. The coating can be applied using sputtering, ion beam deposition or an equivalent technique. While the ring electrodes may be configured as mono-polar or bipolar ring electrodes and it is understood that any number or combinations of uni- and bi-polar ring electrodes may be used as needed or appropriate.

In use, a suitable guiding sheath is inserted into the patient with its distal end positioned in the pericardial sac using a subxiphoid approach. An example of a suitable guiding sheath for use in connection with the present invention is the Preface™. Braiding Guiding Sheath, commercially available from Biosense Webster, Inc. (Diamond Bar, Calif.). For insertion into the guiding sheath, the temperature sensing array 17 of the catheter 10 is rolled up as shown in FIGS. 7A and 7B. The distal ends of the finger members 122 of the temperature sensing array 117 of the catheter 100 (FIG. 8) are gathered together and inserted into the guiding sheath. The circular temperature sensing array 217 of the catheter 200 (FIG. 10) is straightened and fed into the guiding sheath. So inserted, the temperature sensing catheter in use is then fed through the guiding sheath until the temperature sensing array is near the tissue treatment site, generally opposite of ablation electrode(s) of the ablation catheter 84, as shown in FIG. 1. The guiding sheath is pulled proximally, exposing the array which allows the array to resume its neutral deployed configuration under its shape memory and placed on the epicardium 89.

In positioning the array, the user uses the actuator 16a to control puller wires 24 for bidirectional deflection of the intermediate section 14 which moves the array in a sweeping side to side motion. Where the temperature sensing catheter 200 is in use, the user may also use the actuator 16b to control puller wire 222 for tightening the array 217 for an inward spiral configuration to place distal temperature sensing location 50a at an inner or center position relative to the surrounding temperature sensing locations 50b, as shown in FIG. 10.

It is understood that the temperature sensing catheter of the present invention is placed in pericardial space during atrial and/or ventricular ablation procedures. Optionally, an electrophysiology mapping system, such as Carto® 3 (Biosense Webster), may be used to visualize the catheter relative to the heart's anatomy. As illustrated in FIG. 1, the temperature sensing array of the catheter is positioned approximately opposite to the endocardial ablation site, as defined by the location of the ablation electrode during RF ablation. During an ablation, the array can detect an increase in temperature resultant from RF delivery. When the catheter measures the temperature of irreversible damage (approx. 50 C), conventional tissue necropsy understanding is that a transmural lesion has been created in that location. In any event, the catheter can monitor any temperature desired.

The catheter may also be used to determine the tissue thickness at the ablation site in conjuction with the mapping system calculating the distance between tip of the ablation catheter 84 and the nearest portion of the present catheter. During the ablation, the array 17 of temperature sensors and their positions relative to the location sensor 32 may be used in an algorithm to estimate the current dimensions of the lesion while it is being created. The algorithm using, for example, pre-determined settings in the mapping system from manufacturing specifications of the temperature array, is based on the positions and temperature readings of an array of temperatures in the pericardial sac. This algorithm may also include other parameters, such as temperature, power, duration, contact force of ablation electrode, impedance, stability, and local tissue thickness. Alternatively, the ablation catheter may be used on the epicardium in the pericardial sac, whereas the present catheter with the temperature sensor array is used on the endocardium.

In addition, the catheter may include a safety feature to provide an alert to the user of a particular temperature threshold and/or terminate or reduce RF power automatically. This may reduce the potential of collateral tissue and organ damage during ablation procedures.

The ring electrodes 126 may be used for mapping. The ring electrodes also permit measurement of the electrical activity surrounding the ablation site so that the catheter can provide real-time and continuous feedback of the potential recordings or electrograms (ECUs) of the epicardial tissue as ablation is performed. Thus, ECG on the catheter can aid in determining lesion effectiveness. This would be especially helpful in areas of thick wall (such as the ventricle), as the ECG signal may attenuate on the ablation catheter because the area surrounding the ablation electrode is dead, but deep in the wall the signal is still transmitting which would be sensed by the ECG of the temperature sensing catheter.

The catheter of the present invention as used in the pericardial cavity can also aid in determining wall thickness at the point of ablation, by measuring the distance between the electrode(s) on the catheter and ablation electrode(s) of the ablation catheter via an EP Navigation System, or via direct signal communication between both electrodes (e.g., magnetic signal or signal to power ratios). The resulting data is presented to the user to aid in selecting ablation parameters for lesion creation, including, but not limited to, power, time, force, temperature, etc.

Positioning of the temperature sensing locations on the catheter of the present invention in the pericardial cavity opposite the wall of the ablation electrode is accomplished using traditional catheter visualization techniques, including fluoroscopy, EP navigation system, ultrasound, etc.

In one embodiment, magnetic members providing magnetic interaction are provided in or near the respective distal ends of the temperature sensing catheter and the ablation catheter. A sheath is used to help guide the temperature sensing catheter in the pericardial cavity to a location near the ablation catheter, and as it enters a range of magnetic attraction the magnetic attraction pulls it into position relative to the ablation catheter. This enables the temperature sensing array to be as close as possible to the ablation electrode, in contact with the epicardial wall, and maintains the array in position during an ablation.

Moreover, where an EP mapping system (e.g., CARTO 3) is appropriately programmed, a monitor of the system advantageously displays the pericardial temperature sensor and/or electrode array on the heart, and color-codes or otherwise indicates the temperature of the array to the user so he/she can monitor tissue temperature during RF delivery. A suitable algorithm enables the system to display on the monitor lesion size on the mapping system based on temperature, impedance, lesion geometry derived from the temperature sensing array, and/or ECG feedback from the array in combination with the same/similar parameters from the ablation catheter. Additionally, a suitable algorithm enables the system to display on the monitor the heart wall in between the ablation catheter and the temperature sensing catheter in the pericardial cavity based on distance therebetween to support other software disclosures discussed herein.

It is further understood that the present invention also includes a temperature sensing catheter used in endocardial space to support an ablation catheter operating in pericardial space, enabling all the same functionality and performance described herein.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A temperature sensing catheter configured to fit in a pericardial cavity between epicardial and pericardial tissue of a heart, comprising:
   an elongated catheter body having a longitudinal axis; and
   a temperature sensing array distal the catheter body and configured to fit in the pericardial sac, the temperature sensing array comprising:
      a first sheet having a first sheet length along the longitudinal axis of the catheter body, and a second sheet having a second sheet length along the longitudinal axis of the catheter body;
      a tubing extending the first and second sheet lengths between the first and second sheets; and
      a plurality of thermocouple wire pairs extending through a lumen in the tubing and having free distal ends extending out of the tubing through openings in a sidewall of the tubing, the distal ends of the thermocouple wire pairs extending between and being anchored between the first and second sheets.

2. The catheter of claim 1, wherein at least one of the first and second sheets comprises a surface configured to contact an area on the epicardial tissue, or in the pericardial cavity.

3. The catheter of claim 1, wherein a shape defined by the first and second sheets and the tubing of the temperature sensing array has a predetermined curvature.

4. The catheter of claim 1, wherein the temperature sensing array further comprises a support frame positioned between the first and second sheets.

5. The catheter of claim 3, wherein the support frame has a generally rectangular configuration.

6. The catheter of claim 1, wherein the first and second sheets are configured to be rolled around the tubing.

7. The catheter of claim 1, wherein the temperature sensing array further includes at least one ring electrode.

8. A temperature sensing catheter configured to fit in a pericardial cavity between epicardial and pericardial tissue of a heart, comprising:
   an elongated catheter body having a longitudinal axis extending along a distal direction within a plane; and
   a temperature sensing array distal the catheter body and configured to fit in the pericardial sac, the temperature sensing array comprising a plurality of finger members extending from a distal end of the catheter body and having proximal and distal ends, the proximal end of each of the plurality of finger members being fixedly mounted on the distal end of the catheter body, all of the plurality of finger members individually extending from the distal end of the catheter to their distal ends in a generally straight line generally along the distal direction within the plane of the longitudinal axis of the catheter body such that all of the plurality of finger members together define a generally planar configuration extending generally along the longitudinal axis of the catheter body, the proximal ends of the plurality of finger members being anchored in a compressed tubular member, the compressed tubular member having a generally oval cross-section so that the plurality of finger members fan out radially from the distal end of the catheter body generally within the plane of the longitudinal axis of the catheter body, each of the plurality of finger members having at least one temperature sensing location.

9. The catheter of claim 8, wherein the oval cross-section of the compressed tubular member has a predetermined curvature.

10. The catheter of claim 8, wherein the oval cross-section of the compressed tubular member has an adjustable curvature.

11. The catheter of claim 8, wherein each finger member has at least one ring electrode.

12. The catheter of claim 8, wherein the plurality of finger members comprises 2 to 8 finger members.

13. The catheter of claim 8, wherein the compressed tubular member has a distal compressed portion defining the generally oval cross-section, and a proximal portion having a generally circular cross-section.

14. The catheter of claim 13, wherein the proximal portion of the compressed tubular member is anchored within a connector tubing at the distal end of the catheter body.

15. The catheter of claim 8, wherein each of the plurality of finger members comprises a tubing having a central lumen and an elongated support member extending through the central lumen in the tubing, and each of the elongated support members of the plurality of finger members stems from a common proximal end.

16. The catheter of claim 15, wherein each of the elongated support members and the common proximal end are formed from a single sheet of material.

17. A temperature sensing catheter configured to fit in a pericardial cavity between epicardial and pericardial tissue of a heart, comprising:
   an elongated catheter body having a longitudinal axis extending and lying within a plane; and
   a temperature sensing array distal the catheter body and configured to fit in the pericardial sac, the temperature sensing array comprising an elongated body configured to adopt a generally planar generally circular configuration, the generally planar generally circular configuration extending and lying within the plane of the longitudinal axis of the catheter body and comprising a proximal portion extending from about 0° to about 270° of the generally planar generally circular configuration and having a plurality of outer temperature sensing locations along the length of the proximal portion, the elongated body also having a distal portion extending from about 270° to about 360° of the generally planar generally circular configuration and comprising an inner temperature sensing location, the distal portion being movable between a first position and a second position, the first position being such that the proximal portion and the distal portion together extend 360° to form the generally planar generally circular configuration, and such that the inner temperature sensing location of the distal portion is in alignment with the generally planar generally circular configuration of the proximal portion such that in the first position a distal end of the temperature sensing array and the inner temperature sensing location of the distal portion lies generally along a circumference of the generally planar generally circular configuration of the proximal portion, and the second position being such that the distal portion extending from about 270° to about 360° of the generally planar generally circular configuration deflects spirally inward of the proximal portion extending from about 0° to about 270° of the generally planar generally circular configuration such that in the second position the distal end of the temperature sensing array and the inner temperature sensing location of the distal portion is at an inner position relative to the proximal portion of the generally planar generally circular configuration such that the inner temperature sensing location is generally centered in the generally planar generally circular configuration and is surrounded at a radial distance from the outer temperature sensing locations of the proximal portion, the first and second positions both extending and lying within the plane of the longitudinal axis of the catheter body.

18. The catheter of claim 17, wherein the temperature sensing array further comprises:
   a puller wire extending through the elongated body of the temperature sensing array, the puller wire having a distal end anchored at or near a distal end of the elongated body of the temperature sensing array, and
   a compression coil surrounding the puller wire, the compression coil having a distal end at or near a proximal end of the distal portion of the elongated body of the temperature sensing array.

19. The catheter of claim 17, wherein the temperature sensing array includes at least one ring electrode on the elongated body.

20. The catheter of claim 17, further comprising an intermediate section between the catheter body and the temperature sensing array, wherein the intermediate section is configured to deflect within the plane.

\* \* \* \* \*